US00PP24082P2

(12) United States Plant Patent
Dümmen

(10) Patent No.: US PP24,082 P2
(45) Date of Patent: Dec. 10, 2013

(54) POINSETTIA PLANT NAMED 'DUEIMSCEARL'

(50) Latin Name: ***Euphorbia pulcherrima* Willd.**
Varietal Denomination: Dueimscearl

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 96 days.

(21) Appl. No.: 13/385,069

(22) Filed: Jan. 31, 2012

(51) Int. Cl.
*A01H 5/00* (2006.01)

(52) U.S. Cl.
USPC ..... Plt./307; Plt./302; Plt./303

(58) Field of Classification Search
USPC ..... Plt./302, 303, 307
See application file for complete search history.

*Primary Examiner* — Susan McCormick Ewoldt
(74) *Attorney, Agent, or Firm* — C. A. Whealy

(57) ABSTRACT

A new and distinct cultivar of Poinsettia plant named 'Dueimscearl', characterized by its upright, outwardly spreading and uniform plant habit; moderately vigorous growth habit; strong and vigorous roots; freely branching habit; large inflorescences with red-colored flower bracts and numerous cyathia; and excellent post-production longevity.

1 Drawing Sheet

Botanical designation: *Euphorbia pulcherrima* Willd.
Cultivar denomination: 'DUEIMSCEARL'.

BACKGROUND OF THE INVENTION

The present invention relates to a new and distinct cultivar of Poinsettia plant, botanically known as *Euphorbia pulcherrima* Willd., and hereinafter referred to by the name 'Dueimscearl'.

The new Poinsettia plant is a product of a planned breeding program conducted by the Inventor in Rheinberg, Germany. The objective of the breeding program is to create Poinsettia plants with attractive flower bract coloration.

The new Poinsettia plant is a naturally-occurring whole plant mutation of a proprietary selection of *Euphorbia pulcherrima* Willd. identified as code number E-19-022, not patented. The new Poinsettia plant was discovered and selected by the Inventor as a single flowering plant from within a population of plants of the parent selection in a controlled greenhouse environment in Rheinberg, Germany in December, 2009.

Asexual reproduction of the new Poinsettia plant by terminal vegetative cuttings in a controlled greenhouse environment in Rheinberg, Germany since January, 2010 has shown that the unique features of this new Poinsettia plant are stable and reproduced true to type in successive generations of asexual reproduction.

SUMMARY OF THE INVENTION

Plants of the new Poinsettia have not been observed under all possible environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Dueimscearl'. These characteristics in combination distinguish 'Dueimscearl' as a new and distinct Poinsettia plant:

1. Upright, outwardly spreading and uniform plant habit.
2. Moderately vigorous growth habit.
3. Strong and vigorous roots.
4. Freely branching habit.
5. Large inflorescences with red-colored flower bracts and numerous cyathia.
6. Excellent post-production longevity.

Plants of the new Poinsettia differ primarily from plants of the parent selection in flower bract color as plants of the new Poinsettia have brighter red-colored flower bracts than plants of the parent selection.

Plants of the new Poinsettia can be compared to plants of *Euphorbia pulcherrima* Willd. 'Fiscor', disclosed in U.S. Plant Pat. No. 9,364. In side-by-side comparisons conducted in Rheinberg, Germany, plants of the new Poinsettia differed primarily from plants of 'Fiscor' in the following characteristics:

1. Plants of the new Poinsettia had smaller flower bracts than plants of 'Fiscor'.
2. Inflorescences of plants of the new Poinsettia had more cyathia than inflorescences of plants of 'Fiscor'.

BRIEF DESCRIPTION OF THE PHOTOGRAPH

The accompanying photograph illustrates the overall appearance of the new Poinsettia plant showing the colors as true as it is reasonably possible to obtain in colored reproductions of this type. Colors in the photograph may differ slightly from the color values cited in the detailed botanical description which accurately describe the colors of the new Poinsettia plant.

The photograph comprises a side perspective view of a typical flowering plant of 'Dueimscearl' grown in a container.

DETAILED BOTANICAL DESCRIPTION

The aforementioned photograph and following observations and measurements describe plants grown in Rheinberg, Germany during the summer in a glass-covered greenhouse and under environmental conditions and cultural practices which approximate those generally used in commercial Poinsettia production. During the production of the plants, day and night temperatures averaged 22° C. and light levels were about 4,500 lux. Measurements and numerical values represent averages for typical flowering plants. Single plants were grown in 12-cm containers and were pinched one time three weeks after planting the cuttings. Plants were 16 weeks old when the photograph and the detailed description were taken. In the following description, color references are made to The Royal Horticultural Society Colour Chart, 1995 Edition, except where general terms of ordinary dictionary significance are used.

Botanical classification: *Euphorbia pulcherrima* Willd. 'Dueimscearl'.

Parentage: Naturally-occurring whole plant mutation of a proprietary selection of *Euphorbia pulcherrima* Willd. identified as code number E-19-022, not patented.

Propagation:

*Type.*—Terminal vegetative cuttings.

*Time to initiate roots, summer.*—About five days at 20° C.

*Time to initiate roots, winter.*—About seven days at 20° C.

*Time to produce a rooted young plant, summer.*—About three weeks at 20° C.

*Time to produce a rooted young plant, winter.*—About four weeks at 20° C.

*Root description.*—Fine, fibrous; white in color.

*Rooting habit.*—Freely branching; dense.

Plant description:

*Plant habit and form.*—Upright, outwardly spreading and uniform plant habit; broad inverted triangle, mounding; large inflorescences positioned above the foliar plane; moderately vigorous growth habit.

*Plant height.*—About 22 cm.

*Plant diameter or spread.*—About 34 cm.

*Lateral branch description.*—Quantity: Freely branching habit, about six to seven lateral branches develop after pinching. Length: About 18 cm. Diameter: About 5 mm. Internode length: About 1.4 cm. Strength: Moderately strong. Texture: Smooth, glabrous. Color: Close to 137A.

*Foliage description.*—Arrangement: Alternate, simple. Length: About 11.1 cm. Width: About 7.9 cm. Shape: Ovate. Apex: Apiculate. Base: Obtuse. Margin: Lobed; dentate. Venation pattern: Pinnate. Texture, upper surface: Smooth, glabrous. Texture, lower surface: Rugose, glabrous. Color: Developing leaves, upper surface: Close to 137A. Developing leaves, lower surface: Close to 138A. Fully expanded leaves, upper surface: Close to 139A; venation, close to 146A. Fully expanded leaves, lower surface: Close to 137A to 137B; venation, close to 146B to 146C. Petiole: Length: About 6.1 cm. Diameter: About 3 mm. Texture, upper and lower surfaces: Smooth, glabrous. Color, upper and lower surfaces: Close to 187A to 187B.

Inflorescence description:

*Inflorescence type and habit.*—Inflorescences are compound corymbs of cyathia with flower bracts subtending the cyathia; one inflorescence per lateral branch with inflorescences positioned above and beyond the foliar plane.

*Fragrance.*—None detected.

*Natural flowering season.*—Plants flower naturally during the autumn and winter under long nyctoperiod conditions; inflorescence initiation and development can be induced under artificial long nyctoperiod conditions; early flowering habit, response time is about eight weeks.

*Post-production longevity.*—Excellent post-production longevity; plants of the new Poinsettia maintain good substance and bract color for about twelve weeks under interior conditions.

*Inflorescence size.*—Diameter: About 16.5 cm. Height (depth): About 4 cm.

*Flower bracts.*—Quantity per inflorescence: About 15. Length: About 8.5 cm. Width: About 6.2 cm. Shape: Ovate. Apex: Apiculate. Base: Obtuse. Margin: Entire; dentate. Texture, upper surface: Glabrous; smooth. Texture, lower surface: Glabrous; rugose. Venation pattern: Pinnate. Color: Developing bracts, upper surface: Close to 46A. Developing bracts, lower surface: Close to 53B. Transitional bracts, upper surface: Close to 46A to 46B. Transitional bracts, lower surface: Close to 46A to 46B. Fully developed bracts, upper surface: Close to 46A to 46B; venation, close to 46A to 46B; color becoming closer to 46B to 46C with development. Fully developed bracts, lower surface: Close to 46A to 46B; venation, close to 46A to 46B; color becoming closer to 46C to 46D with development. Bract petiole: Length: About 1.3 cm. Diameter: About 2 mm. Texture, upper and lower surfaces: Smooth, glabrous. Color, upper and lower surfaces: Close to 53A.

*Cyathia.*—Quantity per corymb: Numerous, about 15. Length: About 8 mm. Width: About 5 mm. Shape: Ovoid. Color, immature: Inner surface: Close to 143C. Outer surface: Close to 143B. Color, mature: Inner surface: Close to 143B. Outer surface: Close to 143B to 143C. Nectaries: Quantity per cyathium: One. Length: About 4 mm. Diameter: About 1 mm. Color, inner surface: Close to 17A. Color, outer surface: Close to 17C.

*Peduncles.*—Length: About 4 mm. Diameter: About 1 mm. Strength: Strong. Texture: Smooth, glabrous. Color: Close to 143C.

*Reproductive organs.*—Stamens: Quantity per cyathium: About ten. Filament length: About 7 mm. Filament color: Close to 53A. Anther shape: Oval. Anther length: About 0.5 mm. Anther color: Close to 187A to 187B. Amount of pollen: Abundant. Pollen color: Close to 9A. Pistils: Quantity per cyathium: One. Pistil length: About 1 cm. Style length: About 2 mm. Style color: Close to 144B. Stigma shape: Crested. Stigma color: Close to 59A to 59B. Ovary color: Close to 144A. Seeds and fruits: Seed and fruit production have not been observed on plants of the new Poinsettia.

Disease & pest resistance: Plants of the new Poinsettia have not been shown to be resistant to pathogens and pests common to Poinsettia plants.

Temperature tolerance: Plants of the new Poinsettia have been observed to tolerate temperatures ranging from about 5° C. to about 40° C.

It is claimed:

1. A new and distinct Poinsettia plant named 'Dueimscearl' as illustrated and described.

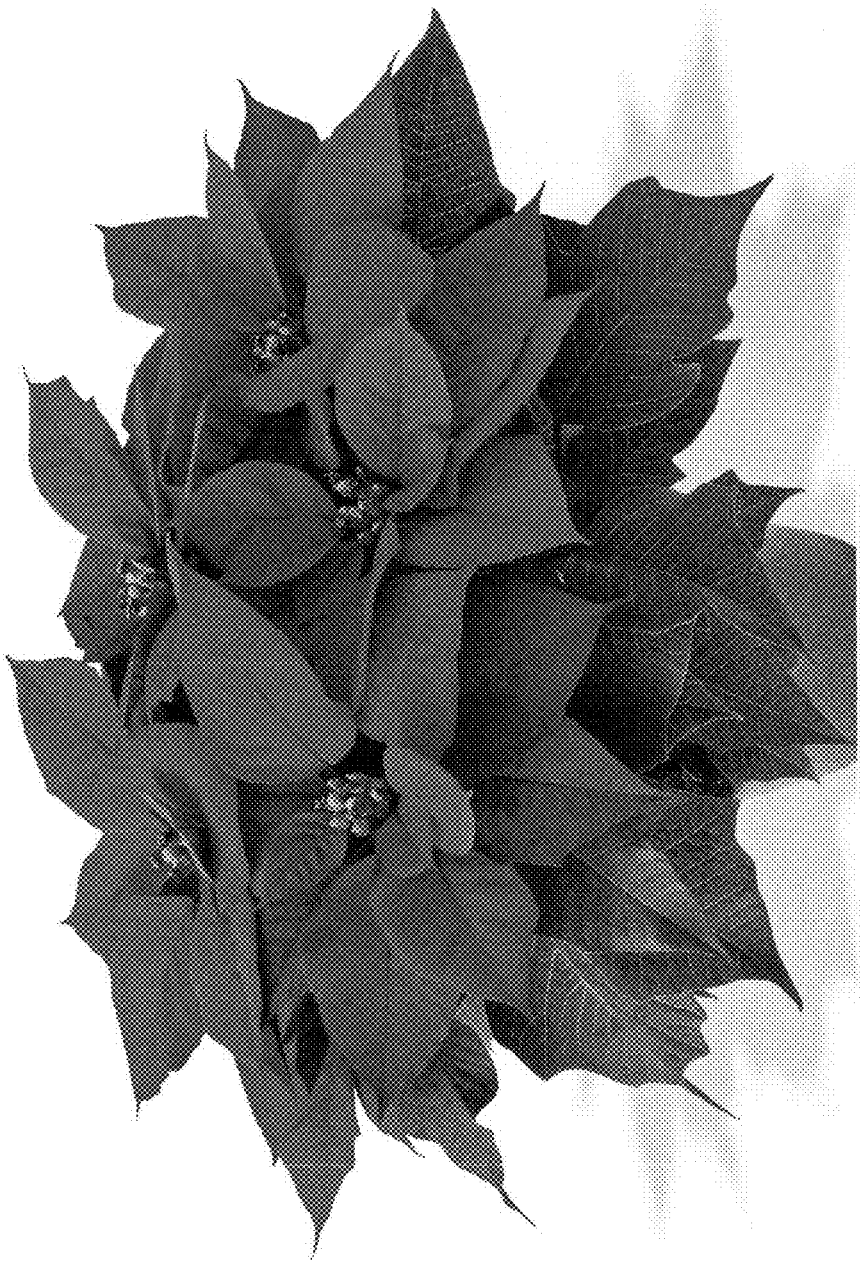

* * * * *